United States Patent [19]

Henderson et al.

[11] Patent Number: 4,496,559
[45] Date of Patent: Jan. 29, 1985

[54] 2-SELENOPYRIDINE-N-OXIDE DERIVATIVES AND THEIR USE AS FUNGICIDES AND BACTERICIDES

[75] Inventors: Richard Henderson, Bethany; Eugene F. Rothgery, North Branford; Hansjuergen A. Schroeder, Hamden, all of Conn.

[73] Assignee: Olin Corporation, Cheshire, Conn.

[21] Appl. No.: 298,679

[22] Filed: Sep. 2, 1981

[51] Int. Cl.$^3$ ............... C07D 213/89; A61K 31/555; A61K 31/44
[52] U.S. Cl. ........................................ 514/188; 546/6; 546/261; 546/290; 514/332; 514/277
[58] Field of Search ............ 546/6, 290, 261; 424/245, 263

[56] References Cited

U.S. PATENT DOCUMENTS

| | | | |
|---|---|---|---|
| 2,694,669 | 11/1954 | Baldwin et al. | 167/87 |
| 2,809,971 | 10/1957 | Bernstein | 546/290 |
| 2,933,432 | 4/1960 | Lichtin | 424/DIG. 4 |
| 3,152,046 | 10/1964 | Kapral | 167/87 |
| 3,269,904 | 8/1966 | Bernstein | 546/6 |
| 3,385,755 | 5/1968 | Seebohm | 424/317 |
| 3,412,033 | 11/1968 | Karsten | 424/65 |
| 3,678,156 | 7/1972 | MacMillan | 424/66 |
| 3,886,277 | 5/1975 | Randebrook | 424/245 |
| 3,965,049 | 6/1976 | Grushkin et al. | 96/1.5 |
| 4,080,329 | 3/1978 | Muntwyler | 546/6 |
| 4,115,313 | 7/1978 | Lyon | 424/70 |
| 4,182,860 | 1/1980 | Naslund | 536/114 |
| 4,185,106 | 1/1980 | Dittmar | 546/290 |
| 4,209,414 | 6/1980 | Holgado et al. | 252/75 |
| 4,401,770 | 8/1983 | Hance | 521/120 |

OTHER PUBLICATIONS

Anon., *Manufacturing Chemist*, 1960, p. 44.
Anon., *American Perfumer*, 71, (3), 43-45, (1958).
Colletti, "Trichology", (Keystone Publications, 1981), p. 25.
Spoor, *J. Soc. Cosmetic Chem.*, 1963, pp. 135-143.
Slinger et al., *Illinois Med. J.* 1954, p. 120.
Gross, *A.M.A. Archives of Dermatology* 78, 92-94.
Scarf et al., *Chem. Abs.* 93, 19942a.
Davis et al., *Chem. Abs.* 84, 100882s.
Tsurkan, *Chem. Abs.* 92, 104953d, (1979).
Lalezari et al., *J. Pharm. Sci.* 67, 1336-8, (1978).
Azerbaev et al., *Chem. Abs.* 85, 77575b.
Kiessling et al., *Chem. Abs.* 85, 125818; (1976).
Kawabe et al., *Chem. Abs.* 68, 1827r, (1967).
Neihof et al., *Arch. Envirn. Contam. Toxicol.* 8, 355-368, (1979).
Mautner, "Symposium at Oak Ridge Institute of Nuclear Studies, Nov. 1-4, 1965", pp. 409-420.
H. Mautner et al., *J. Org. Chem.*, 27, pp. 3671-3673, (1962).
H. R. Yale, Chem. Heterocyclo. Compd., 75, 1975, 14, pt 4, pp. 253-255 and 422-433.
M. Krachov et al., *J. Am. Chem. Soc.*, 87, (4), pp. 892-894.
Olin literature search, (all Chem. Abs. checked).
E. Shaw et al., *J. Am. Chem. Soc.*, 72, p. 4362, (1950).

*Primary Examiner*—Mark L. Berch
*Attorney, Agent, or Firm*—William A. Simons; Thomas P. O'Day

[57] ABSTRACT

Disclosed are selected derivatives of 2-selenopyridine-N-oxide and their use as fungicides and bactericides.

12 Claims, No Drawings

2-SELENOPYRIDINE-N-OXIDE DERIVATIVES AND THEIR USE AS FUNGICIDES AND BACTERICIDES

BACKGROUND OF THE INVENTION

1. Field of the Invention

This invention relates to selected derivatives of 2-selenopyridine-N-oxide and their use as fungicides and bactericides.

2. Description of the Prior Art

Various selenium compounds have been known to possess different types of pesticidal activity such as fungicidal, bactericidal, and the like. In particular, selenium disulfide is a known antidandruff agent. See U.S. Pat. No. 2,644,669, which issued to Baldwin et al. on Nov. 16, 1954.

H. Mautner, S. Chu and C. Lee, in *J. Org. Chem.*, 27, pages 3671-3673 (1962), disclose the synthesis of 2-selenopyridine-N-oxide from 2-bromopyridine-N-oxide and hydrogen selenide. However, the authors do not mention that this compound has any fungicidal or bactericidal activity, nor do they state that this compound may be converted into salts, chelates, or other derivatives.

Separately, the sodium salt and the zinc chelate of 2-mercaptopyridine-N-oxide, along with the di(sulfide) derivative in which two pyridine-N-oxide nuclei are connected by two sulfur atoms, have all been shown to be broad spectrum antimicrobial agents. These 2-mercaptopyridine-N-oxide compounds are especially effective against a wide variety of fungi as well as bacteria. They have found commercial use as industrial biocides in both metalworking fluids and cosmetics. However, they have not been employed commercially as agricultural pesticides because they degrade in the presence of light.

BRIEF SUMMARY OF THE INVENTION

The present invention is directed to, as compositions of matter, selected salts and derivatives of 2-selenopyridine-N-oxide of the formulae (I), (II) and (III):

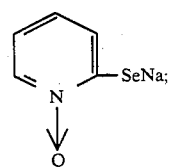
(I)

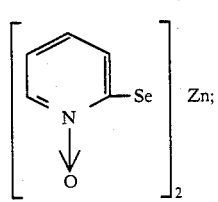
(II)

and

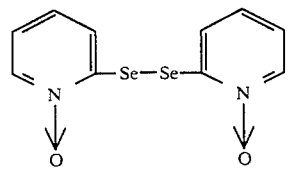
(III)

The present invention is also directed toward the use of these compounds as fungicides and bactericides.

DETAILED DESCRIPTION

The 2-selenopyridine-N-oxide compounds of the present invention may be prepared by reacting the free 2-selenopyridine-N-oxide with either (a) NaOH in a solvent mixture of ethanol and acetone; (b) zinc chloride in $H_2O$/NaOH mixture; and (c) $H_2O_2$ in $H_2O$. These general reactions are illustrated by the following Equations (A), (B), and (C):

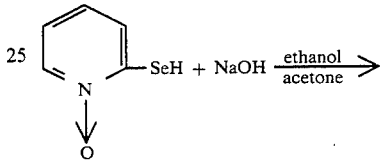

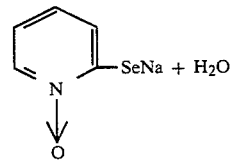
(A)

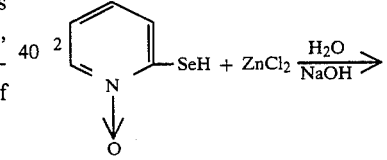

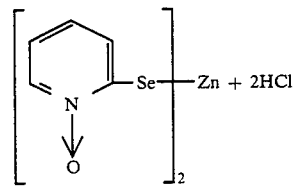
(B)

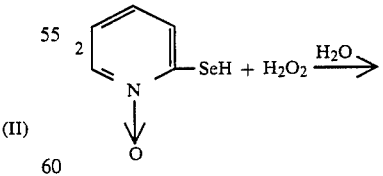

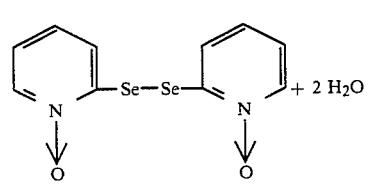
(C)

The precursor, 2-selenopyridine-N-oxide, may be made by reacting sodium hydroselenide (NaHSe) with 2-bromopyridine-N-oxide. However, this free selenopyridine-N-oxide, if left in the open, will decompose readily. However, the salts and derivatives of the present invention are quite stable.

The other reactants, namely NaOH, $ZnCl_2$ or $H_2O_2$, are well known and generally available in commercial quantities.

Any conventional reaction conditions designed to produce sodium salts, zinc chelates and di(selenide)type derivatives from the corresponding free acid may be employed in the synthesis of the present compounds and the present invention is not intended to be limited to any particular reaction conditions. Advantageously and preferably, the reactions are performed with an equimolar amount of 2-selenopyridine-N-oxide and NaOH in the case of the sodium salt and with an about 2:1 molar ratio of the free acid to either $ZnCl_2$ or $H_2O_2$ in the case of the other two compounds. Preferably, a suitable inert solvent is used in these reactions to moderate the speed of these reactions. However, the use of a solvent is only desirable, but not necessary. The reaction temperature and time will both depend upon many factors including the specific reactants and the amounts used. In most situations reaction temperatures may advantageously be from about 30° C. to about 100° C. and reaction times from about 0.5 to about 10 hours may be preferred. The product may be recovered from the reaction mixture by any conventional means; for example, filtration, extraction, slurrying with solvent, recrystallization or the like.

It should be noted that while the reactions illustrated by Equations (A), (B), and (C) are preferred methods for preparing the compounds of the present invention, other synthetic methods may also be employed.

Also, in accordance with the present invention, it has been found that the compounds of Formulae (I), (II) and (III) above may be utilized as effective fungicides or bactericides. In practicing the process of the present invention, fungi or bacteria are contacted with a fungicidally effective amount or bactericidally effective amount of one or more of these compounds. It is to be understood that the terms "fungicidally effective amount" and "bactericidally effective amount" as used in the specification and claims herein are intended to include any amount that will kill or control said fungi or said bacteria, or both, when either employed by itself (i.e., in full concentration) or in sufficient concentrations with a carrier or other substance. Of course, either of these amounts may be constantly changing because of the possible variations in many parameters. Some of these may include: the number and type of fungi or bacteria to be controlled or killed; the type of media to which the present compound can be applied (e.g., seedlings or fully grown plants); degree of effectiveness required; and type of carrier, if any. Generally speaking, applications of an aqueous spray containing at least about 5, more preferably in the range of about 30 to 300, parts per million of the chemical of the present invention may give satisfactory fungi or bacterial control.

This step of contacting may be accomplished by applying this compound to the fungi or bacteria themselves, their habitat, dietary media such as vegetation, crops and the like, including many which these pests may attack.

The above-mentioned compounds of the present invention may be formulated and applied by any conventional methods that include using the compound alone or with a carrier or other substances which may enhance the effectiveness of the chemical or facilitate handling. Moreover, the activity of the present compound may be broadened by the addition thereto of other known pesticides such as other fungicides or bactericides, herbicides, insecticides and the like.

Specific methods of formulating and applying these active compounds include applying them in the form of dusts, dust or emulsion concentrates, wettable powders and concentrates, granulates, dispersions, sprays, solutions and the like.

The dusts are usually prepared by simply grinding together from about 1% to about 15% by weight of the active compound with a finely divided inert diluent such as walnut flour, diatomaceous earth, fullers earth, attaclay, talc or kaolin. Dust concentrates are made in similar fashion excepting that about 16% to about 75% by weight of active compound is ground usually together with the diluent. In practice, dust concentrates are then generally admixed at the site of use with more inert diluent before it is applied to the plant foliage, soil, or animals which are to be protected from fungi or bacteria attack.

Wettable powders are generally prepared in the same manner as dust concentrates, but usually about 1% to about 10% by weight of a dispersing agent, for example, an alkali metal lignosulfonate and about 1% to about 10% of a surfactant, such as a non-ionic surfactant, are incorporated in the formulation. For application to agronomic crops, shrubs, ornamentals and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic or aromatic hydrocarbon or their derivatives. It is preferred that the solvent be odorless and moreover, be inert to the active compound.

It should be clearly understood that the fungicide and bactericide formulations, the ingredients which may make up such formulations other than the active compound, the dosages of these ingredients, and means of applying these formulations may include all known and conventional substances, amounts and means, respectively, that are suitable for obtaining the desired fungicidal or bactericidal, or both, result. And, therefore, such process parameters are not critical to the present invention.

Fungicides and bactericides of the present invention may be effective for the control of the broad class of fungi and bacteria. Specific illustrations of foliar fungi against which fungicidal activity has been shown include bean rust and cucumber anthracnose. Specific illustrations of agricultural bacteria against which bactericidal activity has been shown include Psuedomonas glycinea and Xanthomonas phaseoli.

The following examples further illustrate the present invention. All parts and percentages employed therein are by weight unless otherwise indicated. Yields given are percent molar yields.

EXAMPLE I

2-SELENOPYRIDINE-N-OXIDE

Dilute hydrochloric acid was added dropwise to aluminum selenide (67 g, 90% pure, 0.2 mole) in a 1-liter, 3-neck flask under $N_2$. The $H_2Se$ generated was carried by means of a $N_2$ stream through a $CaCl_2$ drying tower into a solution of sodium ethoxide (12 g, 0.5 g. atoms of Na in 200 ml of ethanol) to form sodium hydroselenide (NaHSe).

2-Bromopyridine N-oxide hydrochloride (81.6 g, 0.32 mole) dissolved in 100 ml of ethanol was neutralized with a solution of sodium ethoxide (7.6 g, 0.33 mole of Na in ethanol). The resulting mixture containing the free N-oxide was added to the above NaHSe solution and refluxed for 1 hr. After cooling, 100 ml of water was added and then the solution acidified with acetic acid. The ethanol was removed on a rotary evaporator leaving a green solid suspended in dilute acetic acid. After filtration, it was recrystalized from ethanol to give yellow-green crystals; mp 70°–72° C.; yield: 25.4 g (45).

Analysis for $C_5H_5NOSe$: Calculated: C, 35.50; H, 2.90; N, 8.05. Found: C, 35.32; H, 3.17; N, 7.94.

EXAMPLE II

SODIUM 2-SELENOPYRIDINE-N-OXIDE

2-Selenopyridine-N-oxide (2 g) was dissolved in a mixture of ethanol and acetone. To this was added an equivalent amount of 50% NaOH solution. The mixture was stirred 15 minutes, then evaporated to dryness. The residue was recrystallized from ethanol and dried overnight in vacuo at 50° C. to give 1.3 g (58%) of product, mp 270°–80° C. (with decomp.).

Analysis for $C_5H_4NNaOSe$: Calculated: C, 30.63; H, 2.05; N, 7.15. Found: C, 30.62; H, 2.22; N, 6.95.

EXAMPLE III

ZINC 2-SELENOPYRIDINE-N-OXIDE

2-Selenopyridine-N-oxide (4 g) was partially dissolved in 150 ml of water (pH 3.2). Solutions of $ZnCl_2$ and dilute caustic were added dropwise to maintain a pH of 6–7 resulting in the formation of a pale yellow solid. Addition was continued until the $ZnCl_2$ solution no longer caused a pH change. The precipitate was recovered by filtration, washed with water and dried in vacuo at 60° C. giving 3.1 g (66%) of product, mp 205°–220° C. (with decomp.).

Analysis for $C_{10}H_8N_2O_2Se_2Zn$: Calculated: C, 29.19; H, 1.96; N, 6.81. Found: C, 29.46; H, 1.92; N, 6.63.

EXAMPLE IV

2,2'-DIPYRIDYLDISELENIDE-N-OXIDE

2-Selenopyridine-N-oxide (5.2 g) was placed in 150 ml of water and 1 ml of 30% $H_2O_2$ was then added. The mixture was stirred 1 hr. at ambient temperature and the resulting product collected by filtration, washed with water and dried at 60° C. in vacuo. Yield: 4.2 g (81%), mp 238°–42° C. (with decomp.).

Analysis for $C_{10}H_8N_2O_2Se_2$: Calculated: C, 34.69; H, 2.33; N, 8.09. Found: C, 34.94; H, 2.51; N, 8.12.

FOLIAR FUNGICIDE SCREEN

The active materials formed in Examples 2, 3, and 4 were then tested for activity as effective fungicides.

A uniform aqueous dispersion of each chemical made in the above examples was first prepared. These dispersions were made by dissolving each chemical in a solution of acetone containing the surfactant TRITON X-155[1] (500 parts per million). Next, this solution was diluted with water (1:9) to obtain a stock solution of 10% by volume acetone and 90% by volume water with 50 ppm TRITON X-155 and the test chemical contained therein. This stock solution was diluted further with water/acetone mix to provide the desired concentration of the test material, if required.

[1] Manufactured by Rohm and Haas of Philadelphia, PA and is a polyether alcohol.

The aqueous solutions containing each chemical were applied to various plants according to the methods stated below. These tests were designed to evaluate the ability of the chemical to protect non-infected foliage and eradicate recently established infection against major types of fungi such as rust and anthracnose that attack above-ground parts of plants.

BEAN RUST

In primary screening, Pinto beans, which were in 2½ inch pots and 9 to 12 days old, were sprayed while rotating the plants on a turntable with an aqueous solution of each chemical of Examples 2, 3, and 4. The aqueous solutions contained 260 parts per million of each active chemical. Simultaneously, the soil in each pot was drenched with aqueous solutions of each chemical in the amount of 25 lb./acre. After the spray deposit had dried, the plants were atomized with a suspension of uredospores [summer spore stage of bean rust (Uromyces phaseoli)] and placed in a moist chamber at 70° F. for 24 hours. After 7 days, the severity of pustule formation was rated on a scale of 0 (no inhibition) to 10 (complete inhibition). See Table I for the results of these tests.

In secondary screening, the same spraying and drenching procedures were followed, except lower concentrations were employed and the spraying and drenching was done separately. After each spraying or drenching, the plants were again atomized with a suspension of uredospores and tested for severity of pustule formation in the same manner. These results are also shown in Table I. The compound of Example 3 was the only one subjected to secondary screening against bean rust.

TABLE I

FUNGICIDAL ACTIVITY AGAINST BEAN RUST

| Compound | Primary Screening | Secondary Screening | | | | | | | |
|---|---|---|---|---|---|---|---|---|---|
| | 25 lb/acre drench & 260 ppm spray | 12.5 lb/acre drench | 6.3 lb/acre drench | 3.2 lb/acre drench | 130 ppm spray | 65 ppm spray | 33 ppm spray | 16 ppm spray | 8 ppm spray |
| Example 2 | 7 | — | — | — | — | — | — | — | — |
| Example 3 | 10 | 4 | 4 | 4 | 10 | 10 | 10 | 8 | 7 |
| Example 4 | 10 | — | — | — | — | — | — | — | — |

CUCUMBER ANTHRACNOSE

For the primary and secondary screening, two week old cucumber plants were atomized with a suspension of cucumber anthracnose spores (*Collectrotrichium lagenarium*) and placed in a moist chamber at 70° F. for 24 hours. In the primary screening, the young plants were then sprayed while rotating the plants on a turntable with an aqueous solution that contained 260 parts per million by weight of the active chemicals of Examples 2, 3, and 4. Simultaneously, the soil in each pot was drenched with aqueous dispersions of each chemical in the amount of 25 lb./acre. After 5 days, the severity of pustule formation was rated on a scale of 0 (no inhibition) to 10 (complete inhibition). See Table II for the results of these tests.

The same procedure was followed with the compound of Example 3 for secondary screening except lower concentrations of that chemical were employed and the spraying and drenching were separated. See Table II for the results of the secondary screening on the compound of Example 3.

TABLE II

FUNGICIDAL ACTIVITY AGAINST CUCUMBER ANTHRACNOSE

| Compound | Primary Screening | Secondary Screening | | | | |
|---|---|---|---|---|---|---|
| | 25 lb/acre drench & 260 ppm spray | 130 ppm spray | 65 ppm spray | 33 ppm spray | 16 ppm spray | 8 ppm spray |
| Example 2 | 0 | — | — | — | — | — |
| Example 3 | 10 | 10 | 10 | 10 | 8 | 6 |
| Example 4 | 0 | — | — | — | — | — |

BACTERICIDE SCREEN

Bacterial suspensions of *Pseudomonus glycinea* and *Xanthomonas phaseoli* were poured separately into a liquified nutrient agar at 45° C. and then into petri dishes to form a thin layer. After the seeded agar was cool, 1 cm discs of #1 Whatman filter paper were dipped separately into the stock solutions prepared for the foliar fungicide screen above which contained 260 ppm of a compound made by either Examples 2, 3, or 4. The treated papers were then placed in the agar for 1-3 days and the "zone of inhibition" was observed and measured. Any candidate causing clear zones was advanced to secondary screening where 130 ppm, 65 ppm, and 33 ppm of the chemical were in the stock solutions. The results of this screening are given in Tables III and IV.

TABLE III

BACTERICIDAL ACTIVITY AGAINST *PSEUDOMONUS GLYCINEA*

| Compound | Primary Screening with 260 ppm Solution | Secondary Screening | | |
|---|---|---|---|---|
| | | 130 ppm Solution | 65 ppm Solution | 33 ppm Solution |
| Example 2 | 5 mm | 6 mm | 5 mm | 2 mm |
| Example 3 | 7 mm | 7 mm | 3 mm | 1 mm |
| Example 4 | 4 mm | — | — | — |

TABLE IV

BACTERICIDAL ACTIVITY AGAINST *XANTHOMONAS PHASEOLI*

| Compound | Primary Screening 260 ppm Solution | Secondary Screening | | |
|---|---|---|---|---|
| | | 130 ppm Solution | 65 ppm Solution | 33 ppm Solution |
| Example 2 | 2 mm | 9 mm | 7 mm | 5 mm |
| Example 3 | 4 mm | 0 mm | 0 mm | 0 mm |
| Example 4 | 9 mm | 0 mm | 0 mm | 0 mm |

What is claimed is:

1. A derivative of 2-selenopyridine-N-oxide selected from the formulae which consisting of:

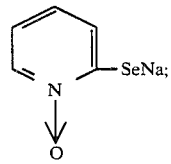

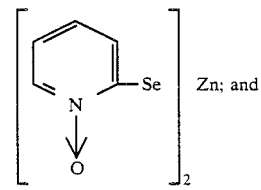

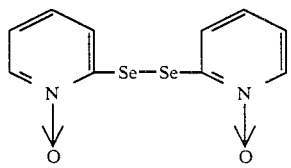

2. The compound of claim 1 having the formula:

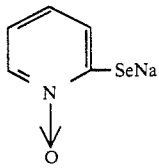

3. The compound of claim 1 having the formula:

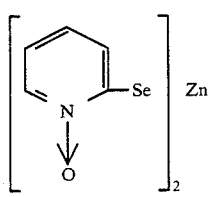

4. The compound of claim 1 having the formula:

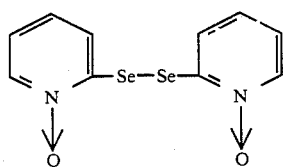

5. The method for controlling fungi which comprises contacting said fungi with a fungicidally effective amount of a compound of claim 1.

6. The method of claim 5 wherein said compound has the formula:

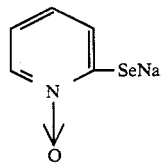

7. The method of claim 5 wherein said compound has the formula:

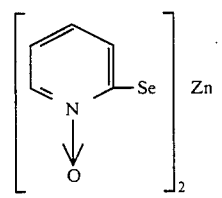

8. The method of claim 5 wherein said compound has the formula:

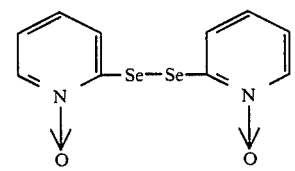

9. The method for controlling bacteria which comprises contacting said bacteria with bactericidally effective amount of a compound of claim 1.

10. The method of claim 9 wherein said compound has the formula:

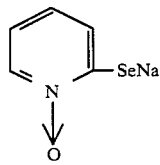

11. The method of claim 9 wherein said compound has the formula:

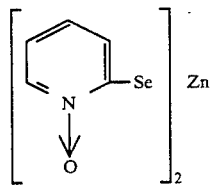

12. The method of claim 9 wherein said compound has the formula:

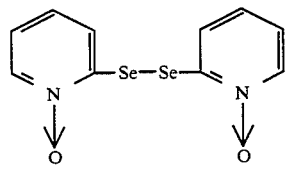

* * * * *